(12) United States Patent
Sorensen et al.

(10) Patent No.: US 6,662,047 B2
(45) Date of Patent: Dec. 9, 2003

(54) PACING MODE TO REDUCE EFFECTS OF ORTHOSTATIC HYPOTENSION AND SYNCOPE

(75) Inventors: Chris Sorensen, Valencia, CA (US); Mark W. Kroll, Simi Valley, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 143 days.

(21) Appl. No.: 09/947,203

(22) Filed: Sep. 5, 2001

(65) Prior Publication Data

US 2003/0045910 A1 Mar. 6, 2003

(51) Int. Cl.⁷ .............................................. A61N 1/365
(52) U.S. Cl. ........................................ 607/18; 607/23
(58) Field of Search ...................... 607/2, 9, 14, 17–19, 607/22–27

(56) References Cited

U.S. PATENT DOCUMENTS

| | | | | | |
|---|---|---|---|---|---|
| 5,040,536 A | * | 8/1991 | Riff | ............................. | 607/23 |
| 5,233,984 A | * | 8/1993 | Thompson | .................... | 607/18 |
| 5,354,317 A | * | 10/1994 | Alt | ............................... | 607/19 |
| 5,913,879 A | * | 6/1999 | Ferek-Petric et al. | .......... | 607/14 |
| 5,919,210 A | * | 7/1999 | Lurie et al. | ..................... | 607/3 |
| 6,026,324 A | * | 2/2000 | Carlson | ........................ | 607/27 |
| 6,259,948 B1 | * | 7/2001 | Florio et al. | ................... | 607/9 |
| 6,466,821 B1 | * | 10/2002 | Pianca et al. | .................. | 607/18 |
| 6,491,639 B1 | * | 12/2002 | Turcott | ........................ | 600/508 |
| 2003/0023279 A1 | * | 1/2003 | Spinelli et al. | ................ | 607/9 |

* cited by examiner

*Primary Examiner*—Kennedy Schaetzle
*Assistant Examiner*—Krister Droesch

(57) ABSTRACT

An implantable cardiac stimulation device is programmed to administer pacing therapy in response to a change in a patient's position and a drop in blood pressure. The stimulation device is equipped with a position sensor to sense a position parameter indicative of when a patient changes from a supine position to an upright position and a pressure sensor to sense a pressure parameter indicative of a patient's blood pressure. The device administers cardiac pacing therapy to the patient based on both the position parameter and the pressure parameter.

56 Claims, 6 Drawing Sheets

PACING MODE TO REDUCE EFFECTS OF ORTHOSTATIC HYPOTENSION AND SYNCOPE

TECHNICAL FIELD

The present invention generally relates to methods and systems for providing cardiac pacing therapy. More particularly, the invention concerns methods and implantable stimulation devices to detect conditions that might give rise to orthostatic hypotension and/or syncope and provide pacing-based cardiac therapies aimed at reducing the effects of orthostatic hypotension and/or syncope.

BACKGROUND

When an individual changes from a horizontal or supine position to a sitting or standing position, the cardiovascular system must make frequent and rapid adjustments to blood pressure and heart rate. When such adjustments are not accomplished, orthostatic hypotension occurs. Orthostasis means upright posture, and hypotension means low blood pressure. Thus, orthostatic hypotension describes the effects caused by low blood pressure when changing from a lying to upright position. Orthostatic hypotension is defined as a decrease of at least 20 mm Hg in systolic blood pressure when an individual moves from the supine to upright position.

The symptoms of orthostatic hypotension include dizziness, faintness, or lightheadedness that appear when standing. Other symptoms that often accompany orthostatic hypotension include chest pain, trouble holding urine, impotence, and dry skin from loss of sweating. Some patients with severe orthostatic hypotension are severely incapacitated.

In addition to orthostatic hypotension, a similar condition that may occur when a patient changes from a supine to upright position is syncope. Syncope describes the effect of temporary impairment of blood circulation to a part of the body. Patients with severe orthostatic hypotension often experience syncope for one to two minutes after sitting up in bed, or after standing.

Two common forms of syncope include vasovagal syncope and carotid sinus syncope. Vasovagal syncope is a condition marked by a sudden drop in heart rate and blood pressure, resulting in fainting. Carotid sinus syncope occurs when reduced blood pressure results in impaired blood flow to the brain, causing brief unconsciousness or fainting. Both vasovagal syncope and carotid sinus syncope are not only unpleasant for a patient, but also potentially dangerous, as fainting may lead to injuries from falls.

This invention arose out of concerns associated with accurately detecting a patient's position changes and timely administering therapy to reduce any effects of orthostatic hypotension and/or syncope.

SUMMARY

An implantable cardiac stimulation device is programmed to administer pacing therapy in response to a change in a patient's position and a drop in blood pressure. The pacing therapy is an increase in the cardiac pacing rate to counteract effects of orthostatic hypotension and/or syncope.

In the described implementation, the cardiac stimulation device is equipped with a position sensor to sense a position parameter indicative of when a patient changes from a supine position to an upright position, such as when moving from a sleeping or reclined posture to a sitting or standing posture. One example of a position sensor is a 3D accelerometer that detects movement in three dimensions.

The cardiac stimulation device is further equipped with a pressure sensor to sense a pressure parameter indicative of a patient's blood pressure. The pressure sensor may be configured to sense pressure directly (e.g., a lead-based pressure sensor that senses pulse pressure or a can-based oxygen sensor) or indirectly (e.g., a photoplethesmic sensor that detects changes in tissue that can be correlated to pressure changes).

The cardiac stimulation device includes a processor operably coupled to the position sensor and the pressure sensor. The processor is programmed to determine when to administer cardiac pacing therapy to the patient based on the position parameter and the pressure parameter. For instance, the processor decides to apply an increased pacing rate effective to treat orthostatic hypotension when the patient experiences both (1) a change in position from a supine position to an upright position and (2) a drop in blood pressure below a predefined threshold.

The processor may further be programmed to apply therapy for treating vasovagal syncope. This therapy is applied when the patient experiences a rapid drop in blood pressure below a threshold level. A position sensor may be used to confirm the onset of vasovagal syncope by detecting that the patient is in a vertical position (e.g., standing or sitting up) and hence should not be experiencing a rapid drop of blood pressure.

In both treatments, the processor is programmed to continue monitoring the pressure sensor. When the patient's pressure rises back above another threshold (which may or may not be the same as the first threshold), the pacing therapy is systematically removed to slowly decay the pacing rate from the increased therapy rate back to the base rate of the patient prior to therapy.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

An implantable cardiac stimulation device is programmed to administer pacing therapy in response to a change in a patient's position and a drop in blood pressure. The stimulation device is equipped with a position sensor to sense a position parameter indicative of when a patient changes from a supine position to an upright position. The device also includes a pressure sensor to sense a pressure parameter indicative of a patient's blood pressure. The device administers cardiac pacing therapy to the patient based on both the position parameter and the pressure parameter.

In one implementation, the device administers pacing therapy effective for treating orthostatic hypotension when the patient experiences both (1) a change in position from a supine position to an upright position and (2) a drop in blood pressure below a predefined threshold. In another implementation, device administers pacing therapy effective for treating syncope, such as vasovagal syncope and carotid sinus syncope, when the patient experiences a rapid drop in blood pressure below a threshold. In both implementations, the pacing therapy is subsequently removed in a systematic manner that slowly decays the pacing rate from the increased therapy rate back to the patient's base rate.

Exemplary Stimulation Device

The techniques described below are intended to be implemented in connection with any stimulation device that is configured or configurable to stimulate or shock a patient's heart.

Figure 1:
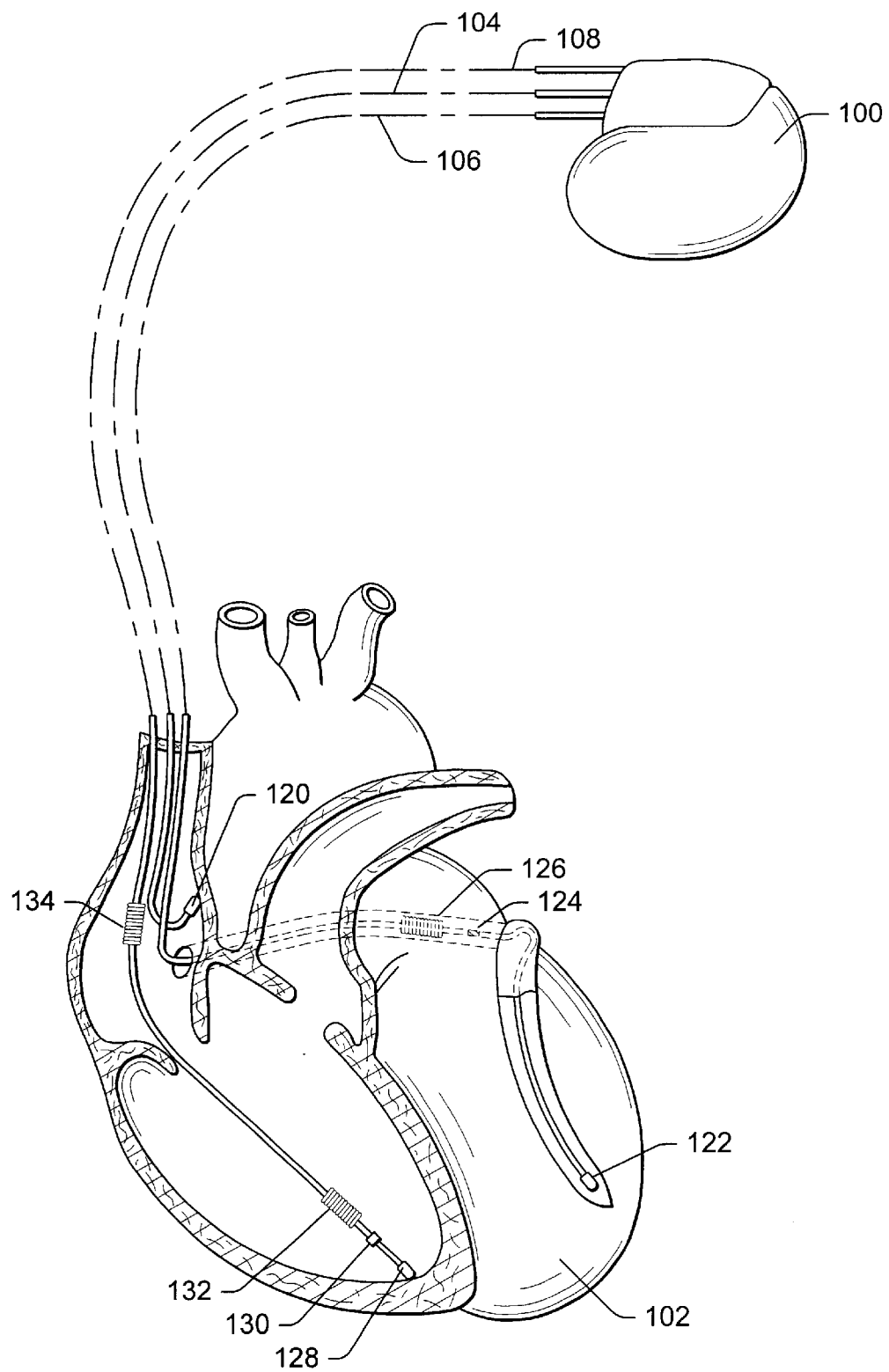
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
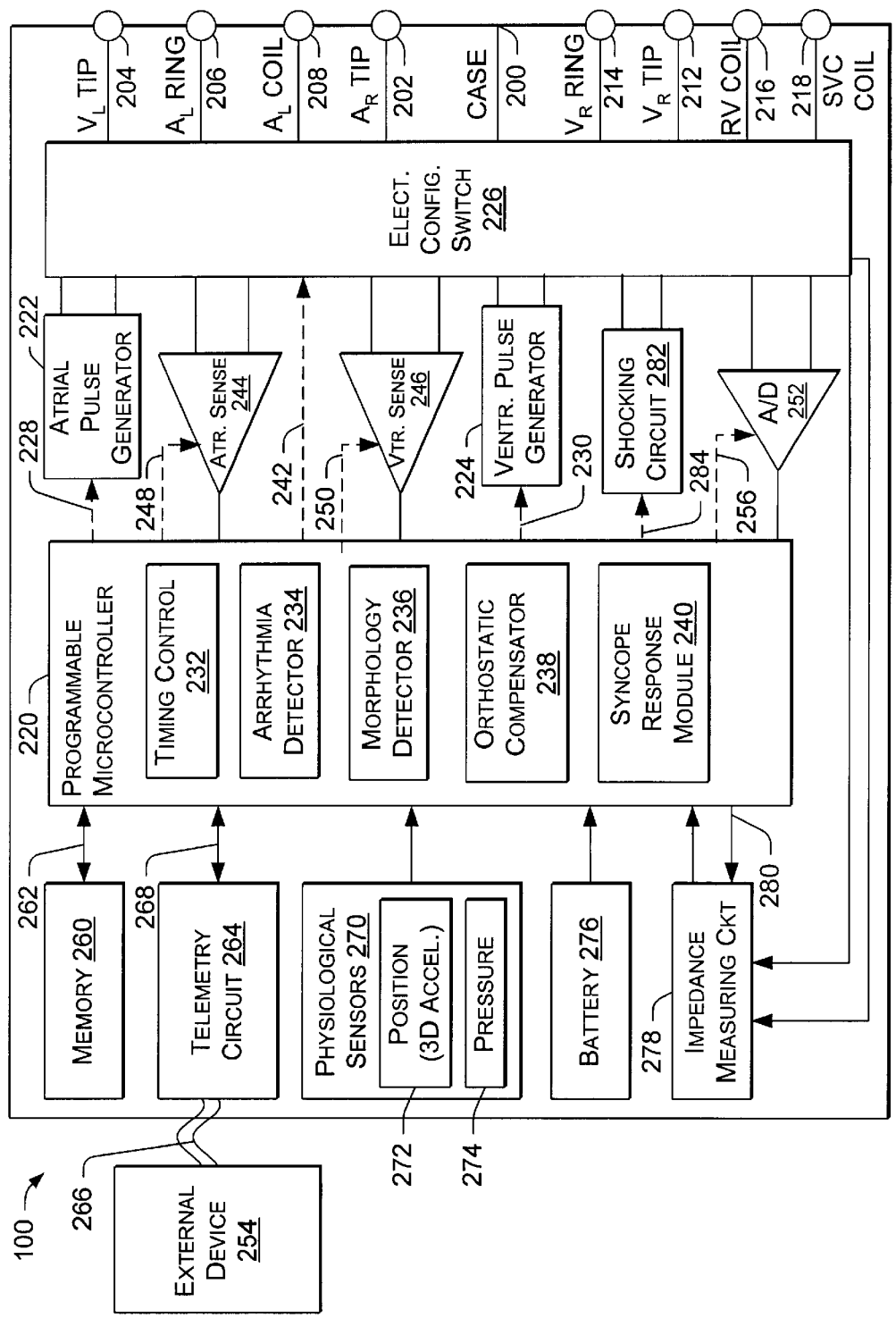
FIG. 2 is a functional block diagram of a multi-chamber implantable stimulation device illustrating basic elements that are configured to provide cardioversion, defibrillation, and pacing stimulation in four chambers of the heart. The implantable stimulation device is further configured to detect onset of orthostatic hypotension and syncope and apply therapy to reduce the effects of orthostatic hypotension and syncope.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The details of the design and operation of the microcontroller 220 are not critical to the described implementations. Rather, any suitable microcontroller 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, an orthostatic compensator 238, and a syncope response module 240. These components can be utilized by the stimulation device 100 for determining desirable times to administer various therapies, including those to reduce the effects of orthostatic hypotension and vasovagal syncope, as will become more apparent below. The components 234–240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiologic sensors 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate and/or minute ventilation, pH of blood, ventricular gradient, and so forth.

Generally, the physiological sensors 270 further include sensors for detecting position or postural changes as well as changes in a patient's blood pressure. Any sensor capable of sensing such physiological parameters, either directly or indirectly, may be used. In particular, the physiological sensors 270 include an activity or position sensor 272 and a pressure sensor 274. The position sensor 272 is mounted within the housing 200 of the stimulation device 100 and is configured to detect movement in the patient's position. The position sensor may be implemented in many ways, including as a 3D accelerometer, a sensor that detects the earth's magnetic or gravitational fields, a MEMs (micro-electro mechanical) device, and the like.

Signals generated by the position sensor 272 are passed to the microcontroller 220 for analysis in determining whether to invoke the orthostatic compensator 238 or the syncope response module 240. The microcontroller 220 monitors the sensor signals for changes indicating that the patient has moved from a supine position to an upright position. For example, the position sensor may generate a signal with little activity while the patient is sleeping or resting. This inactivity may go on for some time. Then, when the patient wakes and sits up, the position sensor will generate signals indicative of this movement. The microcontroller 220 confirms from the sudden change in sensor output following a prolonged period of inactivity that the patient has indeed sat or stood up, and is not merely bending over. The microcontroller 220 uses this information as one condition for deciding when to invoke the orthostatic compensator 238 to apply cardiac pacing therapy for treating orthostatic hypotension.

The pressure sensor 274 is configured to detect changes in blood pressure, such as systolic and/or diastolic blood pressure. The pressure sensor 274 may measure pressure directly or indirectly. One example of a pressure sensor that measures blood pressure directly is a can-based pressure sensor that resides in the housing 200 of the device 100. An example of a can-based pressure sensor is an oxygen ($O_2$) sensor. Another direct pressure sensor is a lead-based pressure sensor that is mounted on a lead within a blood vessel. Such direct sensors can be configured to measure "pulse pressure", which is the difference between the systolic and diastolic blood pressure.

Alternatively, the pressure sensor 274 may be implemented to measure the blood pressure indirectly by monitoring some surrogate physiological parameter that may be correlated to blood pressure. One example of an indirect pressure sensor is a photoplethesmic sensor that delivers light from a light source (e.g., infrared light from a light emitting diode, or LED) to muscle tissue and analyzes the scattered light captured when the light hits and scatters from the tissue (e.g., read by a photodiode). Changes in the scattered light can be used to generate a signal that is proportional to the pulse pressure, and hence can be used to identify changes in blood pressure. An example of a photoplethesmic sensor is described in U.S. patent application Ser. No. 09/543,214, filed Apr. 5, 2000, which is a continuation-in-part of U.S. patent application Ser. No. 09/438,017, filed Nov. 10, 1999.

The microcontroller 220 monitors the pressure sensor signals for changes indicating that the patient's blood pressure has rapidly dropped below a certain threshold. For example, the microcontroller 220 watches for a rapid drop of approximately 20–30 mm Hg in blood pressure within a short period of time (e.g., less than 5 seconds). The microcontroller 220 uses this information as a second condition, in addition to the position data, for deciding when to invoke the orthostatic compensator 238 to apply the pacing therapy for orthostatic hypotension. In the event that the patient experiences both (1) a change in position from a supine position to an upright position and (2) a sudden drop in blood pressure below a predefined threshold, the orthostatic compensator 238 directs a rapid increase in the pacing rate from a base rate (e.g., 50–70 ppm) to a pacing rate suitable for combating the effects of orthostatic hypotension (e.g., 100 ppm). The pacing rate is then slowly decayed over a period of time to return the rate to the base rate.

The microcontroller 220 also uses the pressure data as a condition for determining when to invoke the syncope response module 240 to apply the pacing therapy for vasovagal syncope and carotid sinus syncope. In the event that the patient experiences a sudden drop in blood pressure below a predefined threshold (and the patient is optionally confirmed as being in an upright position), the syncope response module 240 directs a rapid increase in the pacing rate from a base rate (e.g., 50–70 ppm) to a pacing rate suitable for combating the effects of vasovagal syncope and carotid sinus syncope (e.g., 90–110 ppm). The pacing rate is then slowly decayed over a period of time to return the rate to the base rate.

The described implementation can further utilize a "sleep state" or diurnal sensor to detect sleep and wake states. One such sensor is configured to detect activity from which an activity variance can be detected. The sensor is monitored diurnally to detect the low variance in the measurement corresponding to the sleep state. For a complete description of the activity variance sensor, see U.S. Pat. No. 5,476,483 (Bornzin et. al), issued Dec. 19, 1995, which patent is hereby incorporated by reference.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. As one example, the device 100 employs lithium-based batteries.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5–10 J), or high energy (11 to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Orthostatic Hypotension Therapy

Figure 3:
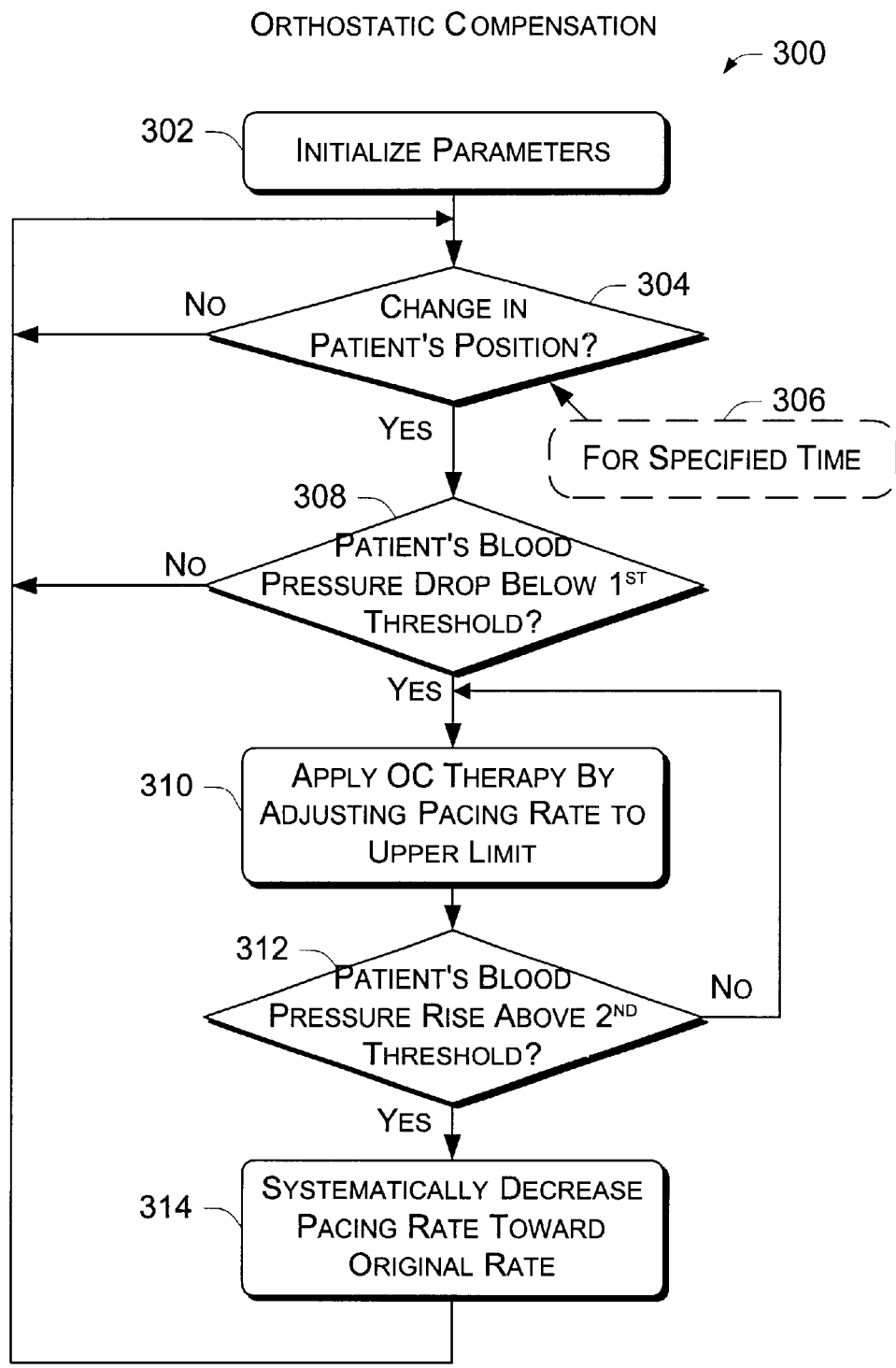
FIG. 3 is a flow diagram of a process to detect conditions that might give rise to orthostatic hypotension and to administer pacing therapy to reduce any effects of orthostatic hypotension.

FIG. 3 shows an exemplary process 300 for detecting conditions that might give rise to orthostatic hypotension and administering pacing therapy to reduce any effects of orthostatic hypotension. The method can be implemented in connection with any suitably configured stimulation device. One specific and non-limiting example of a stimulation device was described above with respect to FIGS. 1 and 2.

In this flow diagram, as well as other flow diagrams described herein, various algorithmic acts are summarized in individual "blocks". Such blocks describe specific actions or decisions that are made or carried out as the process proceeds. Where a microcontroller (or equivalent) is employed, the flow charts presented herein provide a basis for a "control program" or software/firmware that may be used by such a microcontroller (or equivalent) to effectuate the desired control of the stimulation device. As such, the process 300 is implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the inventive subject matter described herein includes not only stimulation devices when programmed to perform the steps described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

At block 302, the parameters used in monitoring orthostatic hypotension are initialized. Such parameters include position information, such as vector data from the three directional axes of the position sensor 272, or time-based position data captured over a period of time, or any other position data indicative of changes in a patient's position. Of particular interest is position data that is used as a benchmark against which the microcontroller is able to detect movement of the patient from a supine position to an upright position. A patient's base blood pressure is also determined for later use as a benchmark to monitor changes in blood pressure that might be caused by changes in a patient's position.

At block 304, the device 100 monitors for changes in a patient's position using the position data output by position sensor 272. More specifically, the microcontroller 220 attempts to detect when the patient changes from a supine position to an upright position, particularly following a prolonged period of inactivity while the patient is in the supine position. Detection may be based on absolute changes in data, such as through use of an absolute position sensor that detects when the patient has reoriented from a horizontal position to a vertical position. In the absence of a postural change indicative of a supine-to-upright movement, the process 300 continues to monitor for position changes in the patient, as represented by the "No" branch from block 304.

To discriminate sudden movements (e.g., bending over) from the desired supine-to-upright change, detection in block 304 may involve an additional time factor 306 that limits detection until a specified time period of prolonged inactivity has elapsed. The time period can be programmed to any desired value that differentiates brief position changes from significant postural changes. With time based detection, the device is first able to confirm that the patient is in the supine position by noting the lack of change in the position data for a prolonged period of time, which is indicative of sleeping or resting. When the patient subsequently sits or stands up for more that a brief period of time, the device confirms the postural change and returns a condition positive from block 304 (i.e., the "Yes" branch from block 304).

At block 308, assuming the patient has changed from a supine to upright position, the device 100 concurrently evaluates whether the patient's blood pressure has dropped below a first threshold. An exemplary first threshold is 30 mmHg in systolic blood pressure and/or 20 mmHg in diastolic blood pressure below the base blood pressure captured during initialization at block 302. As noted above, the blood pressure may be measured directly (e.g., a can-based $O_2$ sensor, or a lead based pressure sensor) or indirectly (e.g., photoplethesmic sensor). The process is particularly interested in sudden pressure drops that occur within a few seconds. If there is no sudden drop in blood pressure below this first threshold, orthostatic hypotension will most likely not occur. Thus, there is no need at this juncture to apply pacing therapy. Instead, the device 100 continues to monitor position changes and blood pressure, as represented by the "No" branch from block 308.

Figure 4:
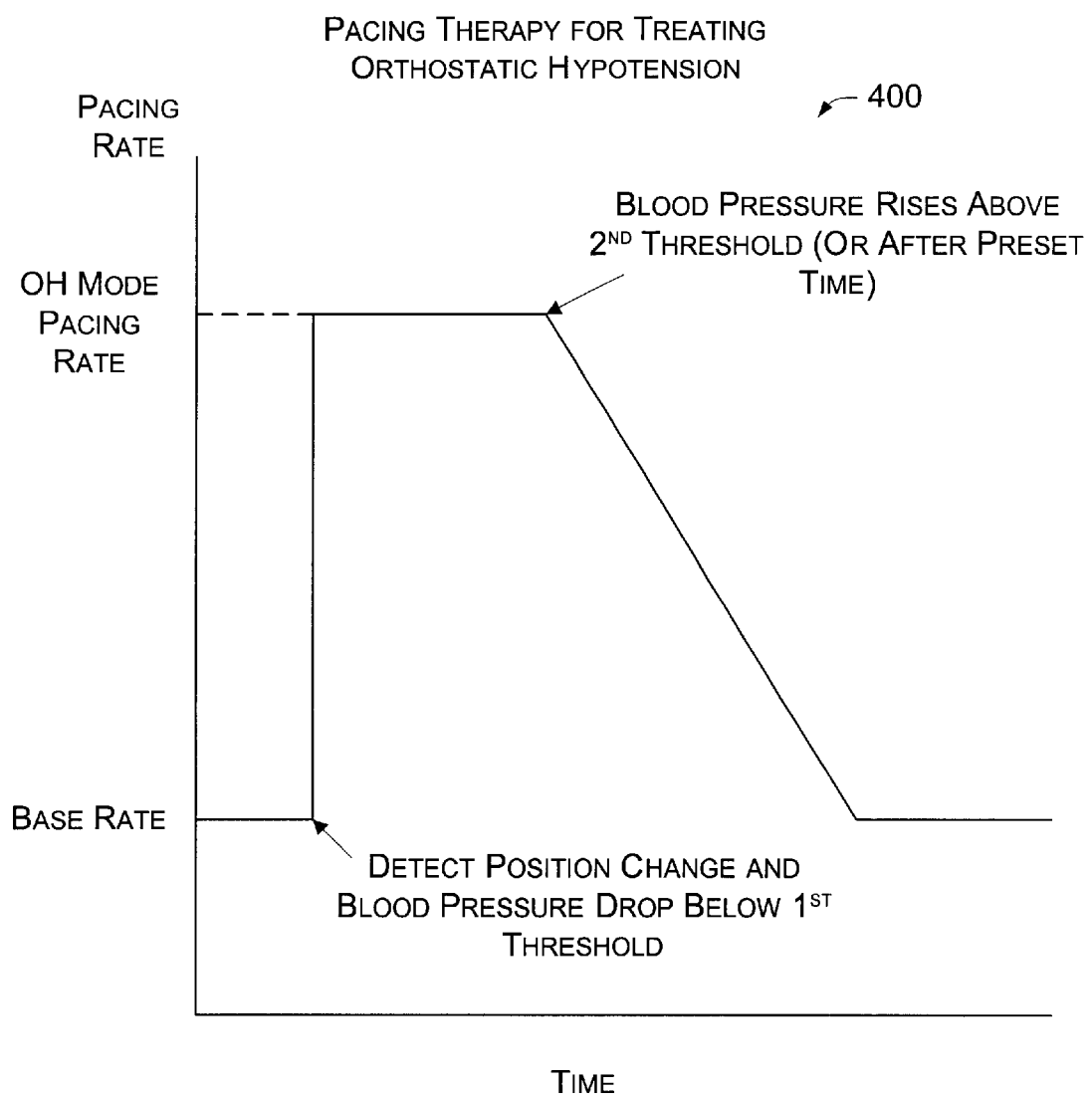
FIG. 4 is an illustration of a pacing therapy effective for treating orthostatic hypotension and syncope.

Assuming that both a position change and a blood pressure drop are detected, the device 100 applies pacing therapy effective for combating orthostatic hypotension (block 310). FIG. 4 shows an exemplary pacing therapy 400 that is triggered upon satisfying both position and pressure conditions. Initially, the pacing rate is at a base rate of, say, 50–70 ppm. When both conditions are met, the pacing rate is adjusted from the base rate to an upper pacing rate programmed into an orthostatic hypotension (OH) mode. As an example, the OH mode pacing rate may be approximately 100 ppm, although these rates are programmable for individual patients. The increased pacing rate causes the heart to beat faster, pumping more blood into the system and hence, increasing blood pressure.

With reference again to FIG. 3, after the therapy is applied, the device 100 continues to monitor the patient's blood pressure (block 312). This monitoring may begin immediately after applying the faster pacing rate for orthostatic hypotension therapy, or it may be delayed for some predefined period of time (e.g., thirty seconds to two minutes). As long as the patient's blood pressure is low (i.e., the "No" branch from block 312), the pacing therapy at the faster pacing rate is continued at block 310. However, as the patient's blood pressure begins to rise back towards its base pressure and crosses over a second threshold level (i.e., the "Yes" branch from block 312), the device 100 systematically begins decreasing the pacing rate toward a reduced rate, such as the original 50–70 ppm (block 314). The pacing rate reduction is performed gradually over a period of time. FIG. 4 illustrates one exemplary decay pattern in which the pacing rate is decreased steadily from the OH mode pacing rate back to the base rate.

It is noted that the second threshold in block 312 used to stop the OH therapy may be the same as the first threshold in block 308 used to trigger the therapy (i.e., 30 mmHg in systolic blood pressure and/or 20 mmHg in diastolic blood pressure below the base blood pressure). Alternatively, the second threshold may be different. As one example, the second threshold that starts the reduction in the pacing rate may be higher than the first threshold to ensure that a sufficient rise in blood pressure has occurred before therapy is gradually withdrawn.

By rapidly applying therapy to a patient who sits or stands up from a supine position and concurrently experiences a rapid reduction blood pressure, the pacing device 100 is able to reduce or eliminate the effects of orthostatic hypotension. The quick response makes it less likely for the patient to experience dizziness, faintness, or lightheadedness when standing.

Syncope Therapy

Figure 5:
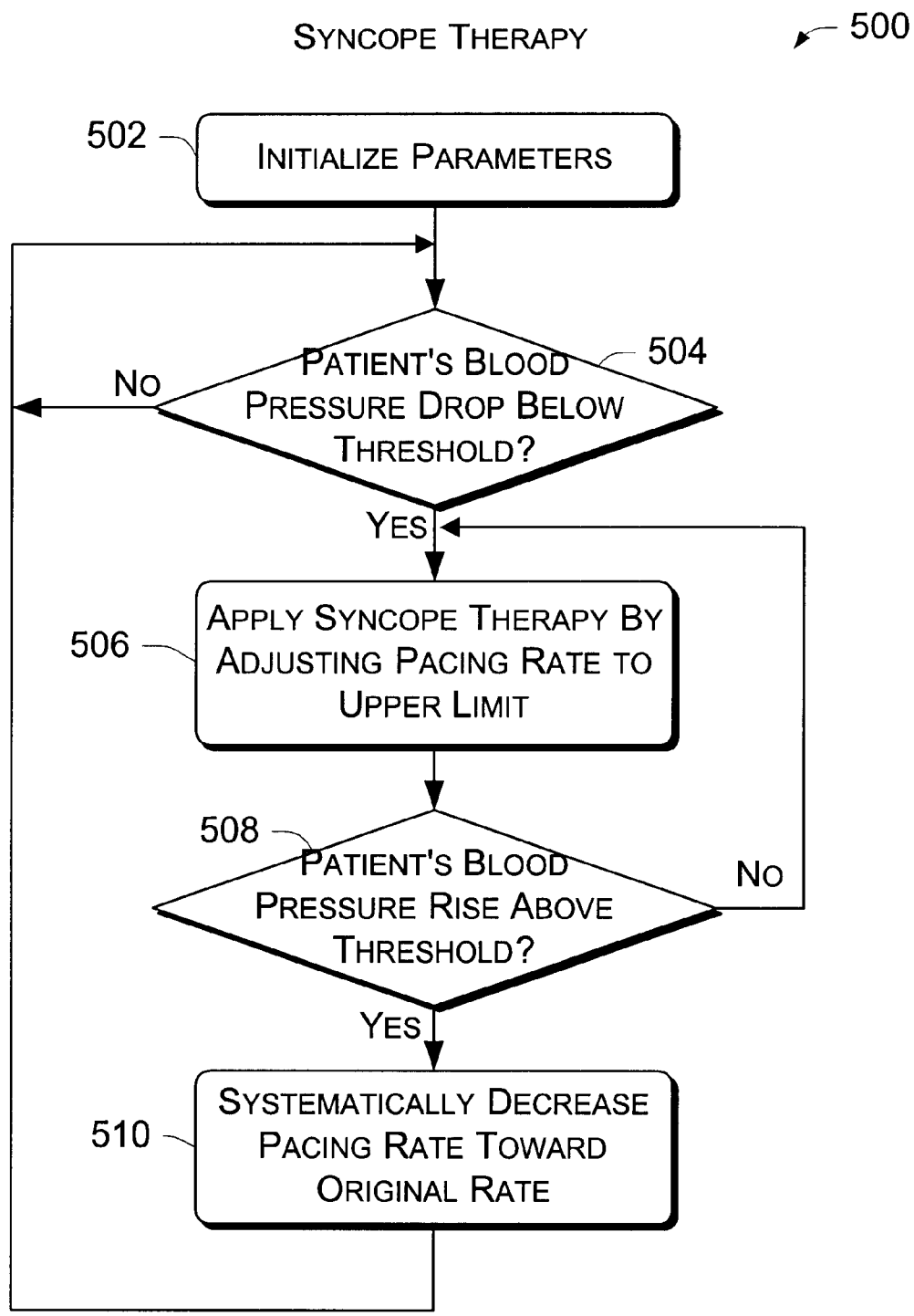
FIG. 5 is a flow diagram of a process to detect conditions that might give rise to syncope and to administer pacing therapy to reduce any effects of syncope.

FIG. 5 shows an exemplary process 500 for detecting conditions that might give rise to syncope—notably, carotid sinus syncope and vasovagal syncope—and administering pacing therapy to reduce any effects of syncope. The method can be implemented in connection with any suitably configured stimulation device. One specific and non-limiting example of a stimulation device was described above with respect to FIGS. 1 and 2. The process 500 may further be implemented as machine-readable instructions stored in memory that, when executed by a processor, perform the various acts illustrated as blocks.

At block 502, the parameters used in monitoring carotid sinus syncope and/or vasovagal syncope are initialized. Such parameters include a patient's base blood pressure, or other surrogate values indicative of blood pressure.

At block 504, the device 100 monitors the patient's blood pressure for a drop below a predefined threshold that is suggestive of an onset of syncope. An exemplary threshold for detecting vasovagal syncope is 30 mmHg in systolic blood pressure and/or 20 mmHg in diastolic blood pressure below the base blood pressure captured during initialization at block 502. A sudden drop of 20–30 mm Hg within a few seconds is suggestive of a syncope condition. If the blood pressure does not drop rapidly below this threshold, the monitoring is continued without application of pacing therapy, as represented by the "No" branch from block 504.

Figure 6:
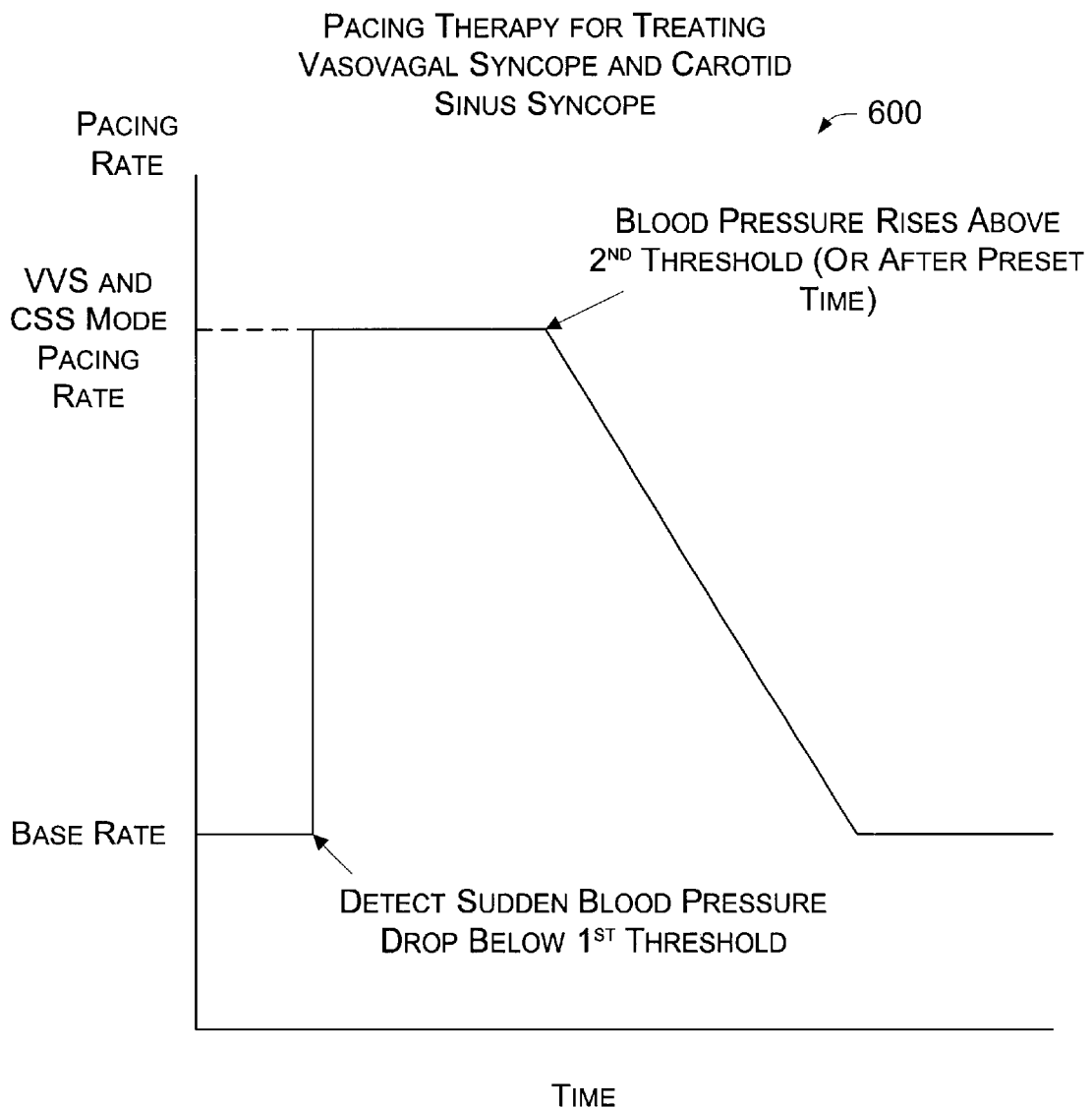
FIG. 6 is an illustration of a pacing therapy effective for treating vasovagal syncope and carotid sinus syncope.

Once a notable rapid drop in blood pressure is detected (i.e., the "Yes" branch from block 504), the device 100 applies pacing therapy effective for combating syncope. For vasovagal syncope, the pacing therapy calls for an increase in the pacing rate from the base rate to an upper limit (block 506). FIG. 6 shows an exemplary pacing therapy 600 that is triggered upon satisfying the pressure drop condition of block 504. The pacing rate is adjusted from the base rate (e.g., 50–70 ppm) to an upper pacing rate programmed into a vasovagal syncope (VVS) or carotid sinus syncope (CSS) mode. As an example, the pacing rate may be raised to a rate of approximately 90–110 ppm. The increased pacing rate causes the heart to beat faster, increasing blood pressure, to thereby counteract syncope.

After the therapy is applied, the device 100 continues to monitor the patient's blood pressure (block 508). As long as the patient's blood pressure stays low (i.e., the "No" branch from block 508), the pacing therapy is continued at block 506. However, as the patient's blood pressure begins to rise back towards its base pressure and crosses over a threshold level (i.e., the "Yes" branch from block 508), the device 100 systematically begins decreasing the pacing rate toward a reduced rate (block 510). The pacing rate reduction is performed gradually over a period of time, as indicated by the therapy 600 in FIG. 6.

It is noted that this process 500 may be modified to include a positional test, similar to the one applied in the orthostatic compensation process at block 304 in FIG. 3. In this modified process, therapy for syncope, such as carotid sinus syncope and vasovagal syncope, is applied only after detecting both a rapid drop in blood pressure and postural change in the patient (e.g., 90° orientation change). This additional condition confirms that the patient is in an upright position and hence, should not be experience such a sudden drop in blood pressure.

By rapidly applying therapy to a patient who experiences a rapid reduction blood pressure, the pacing device 100 is able to reduce or eliminate the effects of vasovagal and carotid sinus syncope. The quick response makes it less likely for the patient to experience brief unconsciousness or fainting.

Conclusion

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac rhythm management device, comprising:
    position sensing means for sensing a change in a patient's position from a supine position to an upright position;
    pressure sensing means for sensing when a patient's blood pressure drops below a predefined threshold; and
    therapy delivery means, responsive to the position sensing means and the pressure sensing means, for generating cardiac stimulating pulses at an increased rate effective to treat orthostatic hypotension when the patient moves from a supine position to an upright position and the patient's blood pressure drops below the predefined threshold.

2. The implantable cardiac rhythm management device of claim 1, wherein the pressure sensing means comprises detecting means for detecting the patient's pulse pressure.

3. The implantable cardiac rhythm management device of claim 1, wherein the pressure sensing means comprises monitoring means for monitoring a physiological parameter that can be correlated with the patient's blood pressure.

4. The implantable cardiac rhythm management device of claim 1, wherein the therapy delivery means systematically reduces the pulse rate following treatment of the orthostatic hypotension.

5. The implantable cardiac rhythm management device of claim 1, wherein the therapy delivery means systematically reduces the rate of pulses when the patient's blood pressure rises above another predefined threshold.

6. A cardiac stimulation device, comprising:
    position sensing means for sensing changes in a patient's position;
    pressure parameter sensing means for sensing a parameter indicative of a patient's blood pressure, the pressure parameter sensing means detecting a drop in the patient's blood pressure below a predefined threshold; and
    therapy administration means, responsive to the position sensing means and the pressure parameter sensing means, for administering cardiac pacing therapy to the patient based on the changes in the patient's position and the patient's blood pressure dropping below the predefined threshold.

7. The cardiac stimulation device of claim 6, wherein the position sensing means comprises sensing means for sensing a change in a patient's position from a supine position to an upright position.

8. The cardiac stimulation device of claim 6, wherein the therapy administration means administers a cardiac pacing therapy effective for combating orthostatic hypotension.

9. The cardiac stimulation device of claim 6, wherein the therapy administration means administers a cardiac pacing therapy effective for combating vasovagal hypotension.

10. A programmable cardiac stimulation device having a memory and a processor, the cardiac stimulation device being programmed to perform tasks comprising:
    administering pacing therapy to a patient when the patient experiences both (1) a change in position from a supine position to an upright position and (2) a drop in blood pressure below a predefined threshold; and
    subsequently removing the pacing therapy in a systematic manner.

11. The programmable cardiac stimulation device of claim 10, wherein the pacing therapy is removed after a predetermined period of time.

12. The programmable cardiac stimulation device of claim 10, wherein the pacing therapy is removed when the patent experiences a rise in blood pressure above another predefined threshold.

13. A cardiac stimulation device comprising:
    a position sensor to sense a position parameter indicative of changes in a patient's position;
    a pressure sensor to sense a pressure parameter indicative of a patient's blood pressure;
    a processor operably coupled to the position sensor and the pressure sensor, the processor being configured to determine when to administer cardiac pacing therapy to the patient based on the position parameter and the pressure parameter, the processor being configured to monitor the pressure parameter during administration of the cardiac pacing therapy and to remove the cardiac pacing therapy in response to a change in the pressure parameter; and
    a pacing generator configured to administer the cardiac pacing therapy as directed by the processor.

14. The cardiac stimulation device of claim 13, wherein the position sensor comprises a 3D accelerometer.

15. The cardiac stimulation device of claim 13, wherein the position sensor is configured to sense a change from a supine position to an upright position.

16. The cardiac stimulation device of claim 13, wherein the pressure sensor comprises a lead-based pressure sensor that senses a pulse pressure.

17. The cardiac stimulation device of claim 13, wherein the pressure sensor comprises an oxygen sensor.

18. The cardiac stimulation device of claim 13, wherein the pressure sensor comprises a photoplethesmic sensor.

19. The cardiac stimulation device of claim 13, wherein the processor determines to administer cardiac pacing therapy when the position sensor detects a change in the patient's position from a supine position to an upright position and the pressure sensor detects a drop in the patient's blood pressure.

20. The cardiac stimulation device of claim 19, wherein the pacing generator increases a pacing rate from a first rate to a higher second rate.

21. The cardiac stimulation device of claim 19, wherein the pacing generator generates a pacing rate effective to counteract effects of orthostatic hypotension.

22. The cardiac stimulation device of claim 19, wherein the pacing generator generates a pacing rate effective to counteract effects of vasovagal syncope.

23. The cardiac stimulation device of claim 19, wherein the pacing generator administers the cardiac pacing therapy for a predetermined period of time.

24. An implantable cardiac rhythm management device, comprising:
  position sensing means for sensing a change in a patient's position;
  pressure sensing means for sensing when a patient's blood pressure drops below a predefined threshold; and
  therapy delivery means for selectively administering pacing therapy to the patient based on the patient's position and the patient's blood pressure, and for monitoring the patient's blood pressure during administration of the pacing therapy and for removing the pacing therapy in response to a change in the patient's blood pressure.

25. The implantable cardiac rhythm management device of claim 24, wherein the pressure sensing means comprises detecting means for detecting the patient's pulse pressure.

26. The implantable cardiac rhythm management device of claim 24, wherein the therapy delivery means systematically reduces the pulse rate following treatment of vasovagal syncope.

27. The implantable cardiac rhythm management device of claim 24, wherein the therapy delivery means systematically reduces the rate of pulses when the patient's blood pressure rises above a predefined threshold.

28. A method comprising:
  determining a position parameter indicative of a change in a patient's position;
  determining a pressure parameter indicative of a patient's blood pressure; and
  selectively administering pacing therapy to the patient based on the position parameter and the pressure parameter;
  wherein the determining a pressure parameter comprises:
    monitoring a patient's blood pressure; and
    detecting a drop in the patient's blood pressure below a predefined threshold.

29. The method of claim 28, wherein the administering comprises increasing a cardiac pacing rate from a first pacing rate to a higher second pacing rate.

30. The method of claim 28, wherein the administering comprises administering a pacing therapy effective to counteract effects of orthostatic hypotension.

31. The method of claim 28, wherein the administering comprises administering a pacing therapy effective to counteract effects of vasovagal syncope.

32. The method of claim 28, further comprising systematically removing the pacing therapy after a predetermined amount of time.

33. One or more computer-readable media having computer-readable instructions thereon which, when executed by a programmable stimulation device, cause the stimulation device to execute the method of claim 28.

34. A method comprising:
  determining a position parameter indicative of a change in a patient's position;
  determining a pressure parameter indicative of a patient's blood pressure; and
  selectively administering pacing therapy to the patient based on the position parameter and the pressure parameter;
  wherein the determining a pressure parameter comprises:
    monitoring a physiological parameter that can be correlated with a patient's blood pressure; and
    detecting a change in the physiological parameter that correlates to a drop in the patient's blood pressure below a predefined threshold.

35. A method of administering pacing therapy for orthostatic hypotension, comprising:
  detecting a change in a patient's position from a supine position to an upright position;
  detecting a drop in a patient's blood pressure below a predefined threshold; and
  adjusting a cardiac pacing rate from a first pacing rate to a second pacing rate effective to counteract effects of orthostatic hypotension in response to detection of the change in the patient's position and the drop in the patient's blood pressure.

36. The method of claim 35, wherein the detecting a change in the patient's position comprises:
  monitoring positional data generated by a 3D accelerometer; and
  detecting, from the positional data, the change from the supine position to the upright position.

37. The method of claim 35, wherein the detecting a drop in the patient's blood pressure comprises:
  directly sensing the patient's blood pressure; and
  ascertaining a drop in the patient's blood pressure.

38. The method of claim 35, wherein the detecting a drop in the patient's blood pressure comprises:
  monitoring a physiological parameter that can be correlated with the patient's blood pressure; and
  ascertaining a change in the physiological parameter that correlates to a drop in the patient's blood pressure.

39. The method of claim 35, wherein the adjusting comprises increasing the cardiac pacing rate from the first pacing rate to the second pacing rate, which is higher than the first pacing rate.

40. The method of claim 35, further comprising adjusting the cardiac pacing rate back toward the first pacing rate.

41. The method of claim 35, further comprising adjusting the cardiac pacing rate back toward the first pacing rate after a predetermined amount of time.

42. The method of claim 35, further comprising:
  detecting a rise in the patient's blood pressure after said adjusting the cardiac pacing rate; and
  in response, adjusting the cardiac pacing rate back toward the first pacing rate.

43. One or more computer-readable media having computer-readable instructions thereon which, when executed by a programmable stimulation device, cause the stimulation device to execute the method of claim 12.

44. A method of administering pacing therapy for vasovagal syncope, comprising:

detecting a change in a patient's position from a supine position to an upright position;

detecting a drop in the patient's blood pressure below a predefined threshold; and adjusting a cardiac pacing rate from a first pacing rate to a second pacing rate effective to counteract effects of vasovagal syncope in response to detection of the change in the patient's position and a drop in the patient's blood pressure below the predefined threshold.

45. The method of claim 44, wherein the detecting comprises monitoring the patient's blood pressure directly.

46. The method of claim 44, wherein the detecting comprises monitoring the patient's blood pressure indirectly by sensing a physiological parameter that can be correlated with the patient's blood pressure.

47. The method of claim 44, wherein the adjusting comprises increasing the cardiac pacing rate from the first pacing rate to the second pacing rate, which is higher than the first pacing rate.

48. The method of claim 44, further comprising adjusting the cardiac pacing rate back toward the first pacing rate.

49. The method of claim 44, further comprising adjusting the cardiac pacing rate back toward the first pacing rate after a predetermined amount of time.

50. The method of claim 44, further comprising:

detecting a rise in the patient's blood pressure above another predefined threshold; and in response, adjusting the cardiac pacing rate back toward the first pacing rate.

51. One or more computer-readable media having computer-readable instructions thereon which, when executed by a programmable stimulation device, cause the stimulation device to execute the method of claim 44.

52. A method comprising:

increasing a pacing rate in a cardiac stimulation device from a first rate to a higher second rate when a patient experiences both (1) a change in position from a supine position to an upright position and (2) a drop in blood pressure below a predefined threshold; and subsequently decreasing the pacing rate back toward the first rate.

53. The method of claim 52, further comprising decreasing the pacing rate after a predetermined period of time.

54. The method of claim 52, further comprising decreasing the pacing rate when the patient experiences a rise in blood pressure above another predefined threshold.

55. One or more computer-readable media having computer-readable instructions thereon which, when executed by a programmable stimulation device, cause the stimulation device to execute the method of claim 52.

56. A method comprising:

determining a position parameter indicative of a change in a patient's position;

determining a pressure parameter indicative of a patient's blood pressure;

selectively administering pacing therapy to the patient based on the position parameter and the pressure parameter;

monitoring the pressure parameter during administration of the pacing therapy;

systematically removing the pacing therapy in response to a change in the pressure parameter.

* * * * *